United States Patent [19]

Robin et al.

[11] Patent Number: 5,103,045
[45] Date of Patent: Apr. 7, 1992

[54] STORAGE-STABLE BIURET POLYISOCYANATES

[75] Inventors: Jean Robin, Lyons; Michel Carlo; Jacques Lavorel, both of Neyron, all of France

[73] Assignee: Rhone-Poulenc Chimie, Courbevoie Cedex, France

[21] Appl. No.: 742,226

[22] Filed: Aug. 6, 1991

Related U.S. Application Data

[63] Continuation of Ser. No. 312,759, Feb. 21, 1989, abandoned, which is a continuation of Ser. No. 92,563, Sep. 3, 1987, abandoned.

[30] Foreign Application Priority Data

Sep. 3, 1986 [FR] France ............................ 86 12524

[51] Int. Cl.$^5$ .......................................... C07C 273/00
[52] U.S. Cl. ...................................... 560/335; 560/351
[58] Field of Search .................................. 560/351, 335

[56] References Cited

U.S. PATENT DOCUMENTS 4,105,686  8/1978  Raes et al. ........................... 560/351
4,625,052 11/1986  Koenig et al. .

Primary Examiner—Alan Siegel
Attorney, Agent, or Firm—Burns, Doane, Swecker & Mathis

[57] ABSTRACT

Storage-stable biuret polyisocyanates useful, e.g., for the production of paints and adhesives, are prepared by reacting at least one aliphatic, alicyclic or arylaliphatic diisocyanate with a biuret-forming reactant, in the presence of an effective amount of at least one organic carboxylic acid and/or anhydride thereof.

13 Claims, No Drawings

STORAGE-STABLE BIURET POLYISOCYANATES

This application is a continuation of application Ser. No. 07/312,759, filed Feb. 21, 1989, abandoned which is a continuation of application Ser. No. 07/092,563, filed Sept. 3, 1987 now abandoned.

BACKGROUND OF THE INVENTION

1. Field of the Invention

The present invention relates to the preparation of polyisocyanates containing a biuret radical, and, more especially, to the preparation of biuret polyisocyanates by reacting an aliphatic, alicyclic or arylaliphatic diisocyanate with a biuret-forming reactant.

2. Description of the Prior Art

Polyisocyanates containing a biuret group have known utility in the production of foams, adhesives and paints.

Among these applications, the use of such polyisocyanates as constituents of paints is becoming increasingly important, especially in the automotive industry.

Paint films produced from aromatic polyisocyanates are also known to turn yellow and crack.

In contrast, paint films prepared from aliphatic, alicyclic or arylaliphatic polyisocyanates retain their properties for very long periods of time and are therefore particularly suitable in the motor vehicle field.

However, the preparation of aliphatic, alicyclic and arylaliphatic polyisocyanates, using diisocyanates and water, presents certain disadvantages.

Thus, according to U.S. Pat. Nos. 3,124,605 and 3,903,127, the reaction of the diisocyanate monomer with water produces polyurea, which precipitates. The reaction between the diisocyanate monomer and water (which is dissolved in small quantities in said diisocyanate) produces a polyisocyanate containing a biuret group. But the reaction of water with small amounts of the diisocyanate monomer that can dissolve therein, results in the production of a polyurea.

As a solution to this problem, the preparation of these polyisocyanates by reacting the diisocyanate monomer with water, at a temperature of at least 70° C. and in a mixture of an ethylene glycol derivative, such as an ethylene glycol methyl ether acetate, and a methyl or ethyl phosphate, has been proposed. See published French Patent application No. 2,382,468.

This process enables the precipitation of polyurea in polyisocyanate to be practically avoided.

However, it also transpires that, when solutions of polyisocyanates containing a biuret group thus prepared are stored for a few days, their viscosity increases, polybiurets are formed, and the free diisocyanate monomer content increases.

SUMMARY OF THE INVENTION

Accordingly, a major object of the present invention is the provision of an improved process for the preparation of polyisocyanates containing a biuret group, which improved process conspicuously mitigates those disadvantages and drawbacks to date characterizing the state of this art.

Briefly, the present invention features the preparation of biuret polyisocyanates having the desired viscosities, and which are storage stable, by reacting at least one aliphatic, alicyclic or arylaliphatic diisocyanate monomer with a biuret-forming reactant, at a temperature of at least 70° C., wherein the reaction is carried out in the presence of at least one carboxylic acid which is soluble in the reaction medium, said at least one carboxylic acid having the general formula (I):

in which:

$R_1$ represents:

a hydrogen atom;

a straight or branched chain alkyl radical containing from 1 to 10 carbon atoms;

a carboxyl radical;

a hydroxycarbonylalkyl radical, the alkyl moiety of which, which may be straight or branched chain, contains from 1 to 9 carbon atoms; or an alkoxycarbonylalkyl radical, the alkyl moiety of which, which may be straight or branched chain, contains from 1 to 9 carbon atoms; and $R_2$ represents:

a hydrogen atom; or an alkyl radical containing from 1 to 4 carbon atoms; with the proviso that $R_1$ and $R_2$ may together form, with the carbon atom from which they depend, an alicyclic ring member containing 5 or 6 carbon atoms, or a substituted such alicyclic ring member bearing:

one or two straight or branched chain alkyl substituents containing from 1 to 4 carbon atoms;

one or two straight or branched chain alkoxy substituents containing from 1 to 4 carbon atoms;

a carboxyl substituent;

an alkoxycarbonyl substituent, the alkoxy moiety of which contains from 1 to 4 carbon atoms;

an acyl substituent containing from 1 to 4 carbon atoms;

or an acetoxy substituent;

or having the general formula (II):

in which:

Ar represents a benzene, pyridine or cyclopentanone ring;

$R_3$ and $R_4$, which may be identical or different, each represent:

a hydrogen atom;

a straight or branched alkyl radical containing from 1 to 4 carbon atoms;

a straight or branched chain alkoxy radical containing from 1 to 4 carbon atoms;

a halogen atom;

an alkoxycarbonyl radical, the alkoxy moiety of which contains from 1 to 4 carbon atoms;

an acyl radical containing from 1 to 4 carbon atoms; and an acetoxy radical;

and/or at least one anhydride of an acid having the formulae (I) or (II).

DETAILED DESCRIPTION OF THE PREFERRED EMBODIMENTS OF THE INVENTION

More particularly according to the present invention, exemplary of the carboxylic acids having the formula (I), representative are, in particular, acetic acid, propionic acid, butyric acid, isobutyric acid, hexanoic acid, octanoic acid, dodecanoic acid, malonic acid, succinic acid, glutaric acid, adipic acid, suberic acid, sebacic acid and cyclohexanecarboxylic acid.

Exemplary of the carboxylic acids having the formula (II), representative are, more particularly, benzoic acid, acetyl-salicylic acid, para-tert-butylbenzoic acid, chlorobenzoic acid, 3,4-dimethoxybenzoic acid, 2-chlorobenzoic acid, 4-chlorobenzoic acid, nicotinic acid, isonicotinic acid and 2-cyclopentanonecarboxylic acid.

Acetic acid, propionic acid, butyric acid, isobutyric acid, benzoic acid and acetic anhydride are more particularly preferred because of their efficiency and their availability on the market.

The amount of carboxylic acid of formulae (I) or (II) and/or of the anhydride of such acid advantageously constitutes from 0.005 to 2% of the weight of the diisocyanate monomer.

It is possible to employ larger amounts, but this is generally of no advantage.

The ratio by weight of carboxylic acid of formulae (I) or (II) and/or anhydride of such an acid: the diisocyanate monomer, preferably ranges from 0.01% to 0.5%.

The biuret-forming reactant employed may be any compound which is capable of reacting with isocyanate groups to form a biuret. Tert-butanol or water, for example, are representative.

Water is the biuret-forming reactant which is the more preferred according to the invention.

The diisocyanate monomers used in the process of the invention are aliphatic diisocyanates, alicyclic diisocyanates and arylaliphatic diisocyanates, the isocyanate groups of which are not directly linked or bonded to an aromatic ring.

Exemplary of such diisocyanate monomers, representative are:
1,3-diisocyanatopropane,
1,4-diisocyanatobutane,
1,5-diisocyanatopentane,
1,6-diisocyanatohexane,
1,4-diisocyanato-2-ethylbutane,
1,5-diisocyanato-2-methylpentane,
1,6-diisocyanato-2,2,4-trimethylhexane,
1,6-diisocyanato-2,4,4-trimethylhexane,
1,2-diisocyanatocyclohexane,
1,4-diisocyanatocyclohexane,
1,2-bis(isocyanatomethyl)cyclobutane,
bis(4-isocyanatocyclohexyl)methane, 3,3,5-trimethyl-5-isocyanatomethyl-1-isocyanatocyclohexane,
1,4-bis(isocyanatomethyl)benzene, and
1,2-bis(isocyanatomethyl)benzene.

The diisocyanate monomers may be employed separately, or in the form of admixtures thereof.

Thus, for example, 1,6-diisocyanatohexane, which is one of the preferred diisocyanate monomers, may be used alone or in admixture, especially with 1,5-diisocyanato-2-methylpentane and/or 1,4-diisocyanato-2-ethylbutane; mixtures of the latter two diisocyanates may also be employed.

The molar ratio of diisocyanate monomer:water may vary over wide limits. However, the molecular weight of the polyisocyanate produced increases with decreasing molar ratio of diisocyanate monomer:water. In general, it is not advantageous to have an excessively high molecular weight or viscosity.

On the other hand, the molecular weight and the viscosity of the polyisocyanate produced decreases with an increasing ratio of diisocyanate monomer:water. However, an excessively high ratio is economically undesirable, as it entails the separation and the recovery of a large amount of diisocyanate monomer.

Therefore, a molar ratio of diisocyanate monomer:water of from 2 to 40 is typically selected. This ratio preferably ranges from 5 to 15.

The temperature at which the reaction between the diisocyanate monomer and water is carried out typically ranges from 70° C. to 200° C.

Higher temperatures do not hinder the reaction, but give rise to undesirable coloration in the final product.

The reaction is preferably carried out at a temperature of from 110° C. to 150° C.

The process is typically carried out in the presence of a solvent or mixture of solvents.

The amount of solvent advantageously constitutes from 10% to 80% by weight of the reaction mixture.

An alkoxyalkane derived, for example, from ethylene glycol (or from ethylene oxide) or from propylene glycol (or from propylene oxide), is advantageously used as the solvent; a carboxylate, in particular an acetate, of an alkoxyalkane or of a diol, may also be used.

The ethylene glycol derivatives described in published French patent application No. 2,382,468 are exemplary.

2-Methoxyethyl acetate, 1,2-dimethoxyethane, 2-ethoxyethyl acetate, ethylene glycol diacetate, 1-methoxy-2-propyl acetate, 2-methoxy-1-propyl acetate, 1-ethoxy-2-propyl acetate and 2-ethoxy-1-propyl acetate are more particularly representative.

The solvent may also be a methyl and/or ethyl ester of phosphoric acid, especially trimethylphosphate, triethylphosphate, dimethyl ethyl phosphate or diethyl methyl phosphate.

The solvents may be employed separately or as mixtures, such as, for example, mixtures of an alkoxyalkane or of an alkoxyalkane carboxylate or of a diol dicarboxylate with a methyl and/or ethyl ester of phosphoric acid.

The process of the invention may also be carried out in the absence of solvent or using small amounts of solvent, without departing from the ambit hereof.

By "small amounts" of solvent are intended amounts representing from 1 to 10 times the weight of water employed.

These amounts preferably represent from 1 to 5 times the weight of water employed.

The purpose of utilizing such small amounts of solvent is to dilute the water and to promote its contact, and therefore its reaction, with the diisocyanate monomer.

In one embodiment of the process of the invention, the reaction is carried out at an absolute pressure greater than or equal to 1.2 bar, with a partial pressure of carbon dioxide of at least 0.2 bar.

In practice, in this embodiment, the apparatus may either be purged beforehand with carbon dioxide and after establishing an absolute initial pressure of at least 1.2 bar, the pressure may permitted to rise during the biuret reaction up to the desired pressure, for example, between 1.2 and 100 bars absolute or, after purging with a dry inert gas, the pressure in the apparatus may be topped with carbon dioxide up to an absolute initial pressure of at least 1.2 bar and the operations continued as mentioned above.

This embodiment may be employed with or without solvent, but its principal advantage is in operating without solvent or with small amounts of solvent, which greatly increases the productivity of the apparatus.

In practice, the process according to the invention may be carried out by charging a suitable apparatus with the diisocyanate monomer(s) (most frequently 1,6-diisocyanatohexane), the carboxylic acid of formulae (I) or (II) or the anhydride of such an acid and, where appropriate, the solvent(s).

After heating, under stirring, at a temperature of from 70° C. to 200° C., the biuret-forming reagent, which is most frequently water, is added.

The carbon dioxide formed may either be permitted to escape, or a carbon dioxide pressure greater than atmospheric pressure, for example 2 to 10 bars, may be maintained.

When the biuret reaction is complete (in general, a few minutes to several hours), the carbon dioxide is degassed if required and the solvent, if present, and the excess diisocyanate, are quickly removed.

A clear biuret, without any precipitate, is obtained. Its viscosity depends on the molar ratio of diisocyanate monomer:biuret-forming reactant selected.

The biuret is stable over time; no precipitation is observed after several months of storage, whereas the free diisocyanate content changes with time much less quickly than in the case of biurets prepared without carboxylic acid.

In order to further illustrate the present invention and the advantages thereof, the following specific examples are given, it being understood that same are intended only as illustrative and in nowise limitative.

EXAMPLES 1 and 2 and CONTROL TRIAL

A 2-liter three-necked round-bottomed flask equipped for stirring and temperature control and with a reflux condenser, was charged with all constituents: 1,6-diisocyanatohexane (HDI)+solvents+water+acid.

The mixture was heated to 130° C. utilizing a heating mantle.

The gas formed at temperatures above 90° C. escaped through the condenser. The temperature (130° C.) was maintained for 3 hours.

The final product (biuret+HDI+solvent) was evaporated using a rotary film evaporator.

The data from these experiments are reported in the following Table:

TABLE

|  | Control trial (without acid) | Example 1 (with acetic acid) | Example 2 (with benzoic acid) |
| --- | --- | --- | --- |
| HDI | 904.5 g | 904.5 g | 904.5 g |
| H$_2$O | 12 g | 12 g | 12 g |
| Solvents (1) | 446 g | 446 g | 446 g |
| Acid | 0 | 0.3 g | 1.0 g |
| Viscosity of biuret at 25° C. (in pascal × s) | 3.8 | 3.8 | 3.4 |
| Stability: HDI % (2) | 1.3 | 0.7 | 0.45 |

(1) solvents: 2-methoxyethyl acetate and ethylphosphate (1:1)
(2) HDI formed after storage for 1 month at 60° C.

A lower viscosity and an improvement in stability were observed then the reaction was carried out in the presence of an acid (at the same HDI:water ratio).

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

what is claimed is:

1. A process for the preparation of a biuret polyisocyanate, comprising reacting at least one aliphatic, alicyclic or arylaliphatic diisocyanate with a biuret-forming reactant, at a temperature of at least 70° C., and in the presence of an effective amount of at least one organic carboxylic acid and/or anhydride thereof, said organic carboxylic acid having the general formula (I):

in which $R_1$ is a hydrogen atom; a straight or branched chain alkyl radical containing from 1 to 10 carbon atoms; a carboxyl radical; a hydroxycarbonylalkyl radical, the alkyl moiety of which may be straight or branched chain, contains from 1 to 9 carbon atoms; or an alkoxycarbonylalkyl radical, the alkyl moiety of which may be straight or branched chain, contains from 1 to 9 carbon atoms; and $R_2$ is a hydrogen atom; or an alkyl radical containing from 1 to 4 carbon atoms; with the proviso that $R_1$ and $R_2$ may together form, with the carbon atom from which they depend, an alicyclic ring member containing 5 or 6 carbon atoms, or a substituted such alicyclic ring member bearing: one or two straight or branched chain alkyl substituents containing from 1 to 4 carbon toms; one or two straight or branched chain alkoxy substituents containing from 1 to 4 carbon atoms; a carboxyl substituent; an alkoxycarbonyl substituent, the alkoxy moiety of which contains from 1 to 4 carbon atoms; or an acetoxy substituent; or having the general formula (II):

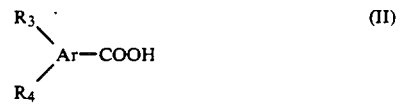

in which Ar is a benzene, pyridine or cyclopentanone ring; and $R_3$ and $R_4$, which may be identical or different, are each a hydrogen atom; a straight or branched chain alkoxy radical containing from 1 to 4 carbon atoms; a halogen atom; an alkoxycarbonyl radical, the alkoxy moiety of which contains from 1 to 4 carbon atoms; an acyl radical containing from 1 to 4 carbon atoms; or an acetoxy radical, wherein the mount of said organic carboxylic acid and/or anhydride thereof is in the range of from 0.005 to 0.5% of the weight of the diisocyanate monomer.

2. The process as defined by claim 1, wherein said biuret-forming reactant comprises water.

3. The process as defined by claim 2, wherein the molar ratio of diisocyanate:water ranges from 2 to 40.

4. The process as defined by claim 1, wherein said carboxylic acid or anhydride thereof comprises acetic acid, propionic acid, isobutyric acid, benzoic acid or acetic anhydride.

5. The process as defined by claim 1, wherein said at least one diisocyanate comprises:
1,3-diisocyanatopropane,
1,4-diisocyanatobutane,
1,5-diisocyanatopentane,
1,6-diisocyanatohexane, 1,4-diisocyanato-2-ethylbutane,
1,5-diisocyanato-2-methylpentane,
1,6-diisocyanato-2,2,4-trimethylhexane,
1,6-diisocyanato-2,4,4-trimethylhexane,
1,2-diisocyanatocyclohexane,
1,4-diisocyanatocyclohexane,
1,2-bis(isocyanatomethyl)cyclobutane,
bis(4-isocyanatocyclohexyl)methane, 3,3,5-trimethyl-5-isocyanatomethyl-1-isocyanatocyclohexane,
1,4-bis(isocyanatomethyl)benzene, and
1,2-bis(isocyanatomethyl)benzene.

6. The process as defined by claim 1, wherein said reaction is carried out in a solvent medium constituting from 20 to 80% by weight of the reaction mixture.

7. The process as defined by claim 6, wherein said solvent medium comprises an alkoxyalkane, alkoxyalkane carboxylate, diol carboxylate or methyl and/or ethyl ester of phosphoric acid.

8. The process as defined by claim 1, wherein said reaction is carried out in the absence of solvent, or in the presence of small amounts of solvent.

9. The process as defined by claim 1, wherein said reaction is carried out at an absolute pressure greater than or equal to 1.2 bar, under a partial pressure of carbon dioxide of at least 0.2 bar.

10. The process as defined by claim 1, wherein said reaction is carried out at a temperature of from 70° C. to 200° C.

11. The process as defined by claim 7, wherein said carboxylic acid of the formulae (I) or (II) and/or anhydride thereof comprises from 0.01% to 0.5% by weight of said at least one diisocyanate.

12. The process as defined by claim 3, wherein the molar ratio of diisocyanate:water ranges from 5 to 15.

13. A storage-stable, essentially polybiuret-free biuret polyisocyanate produced by the process as defined by claim 1.

* * * * *